United States Patent
Han

(10) Patent No.: US 6,907,299 B2
(45) Date of Patent: Jun. 14, 2005

(54) ELECTRODES FOR A TRANSCUTANEOUS ELECTRICAL NERVE STIMULATOR

(76) Inventor: Shu-Chang Han, 8F-3, No. 29, Sec. 3, Chung-Shan N. Rd., Taipei (TW)

( * ) Notice: Subject to any disclaimer, the term of this patent is extended or adjusted under 35 U.S.C. 154(b) by 434 days.

(21) Appl. No.: 10/155,678

(22) Filed: May 24, 2002

(65) Prior Publication Data

US 2003/0220679 A1 Nov. 27, 2003

(51) Int. Cl.[7] .............................................. A61N 1/04
(52) U.S. Cl. ..................... 607/152; 607/142; 600/372; 600/391; 600/395
(58) Field of Search ................................ 607/115, 142, 607/152; 600/372, 382, 391, 395

(56) References Cited

U.S. PATENT DOCUMENTS

| | | | | |
|---|---|---|---|---|
| 5,265,579 A | * | 11/1993 | Ferrari | 600/385 |
| 5,571,165 A | * | 11/1996 | Ferrari | 607/142 |
| 5,727,549 A | * | 3/1998 | Suda et al. | 600/393 |
| 6,600,957 B2 | * | 7/2003 | Gadsby | 607/142 |

* cited by examiner

*Primary Examiner*—Carl Layno
(74) *Attorney, Agent, or Firm*—Thomas E. Sisson; Jackson Walker L.L.P.

(57) ABSTRACT

A TENS electrode formed by multiple layers, wherein a layer of self-adhesive conductive gel base onto which the conductive body is mounted. An isolating pad mounted on the conductive body, and a lead wire securely sandwiched in between the conductive body and the isolating tape. The conductive body is made of carbon fiber to provide the advantages of low impedance and superior softness. Further, since the conductive body is made of nonmetallic material, any electromagnetic interference is avoided.

1 Claim, 3 Drawing Sheets

ELECTRODES FOR A TRANSCUTANEOUS ELECTRICAL NERVE STIMULATOR

BACKGROUND OF THE INVENTION

1. Field of Invention

The present invention relates to a TENS (Transcutaneous Electric Nerve Stimulator) electrode that utilizes carbon fiber as the conductive body, hence outshines its peer products with its high conductivity and exceptional softness.

2. Related Art

The Transcutaneous Electrical Nerve Stimulator (TENS), one of the most important contrivances used by the physiotherapists in the world, puts out prescribed electrical currents to stimulate the nerves or muscle tissues and treats many physical problems. The TENS electrodes are essential to a TENS, because only through these electrodes can the prescribed electrical currents be directed into the body.

FIG. 3 shows the structure of a conventional TENS electrode. A layer of self-adhesive conductive gel (60), the conductive body (61) mounted on the self-adhesive conductive gel (60), an isolating tape (62) mounted on the conductive body (61). A lead wire (70) with the first terminal electrically provided between the conductive body (61) and the isolating tape (62). The self-adhesive conductive gel (60) is made of electrically conductive material to direct electrical current into the body. The self-adhesive conductive gel (60) is to be positioned at the treatment site on the skin. The second terminal (71) of the lead wire (70) connects the TENS. Conventionally, the material to fabricate the conductive body (61) is chosen from aluminum foil, stainless steel fiber cloth or the carbon film.

When the conductive body (61) is made of aluminum foil, high conductivity will be expected. However, the aluminum foil is too hard to go with the protrude body parts such as the knees or the elbows, and does not always fit in with the contour of the human body. Further, the bond force between the conductive body (61) and the self-adhesive conductive gel (60) is weak because of the low adhesion force of metal, i.e. the aluminum foil. So when such electrodes are removed from the body, the conductive body (61) and the self-adhesive conductive gel (60) are often separated. Another downside of the aluminum foil electrodes is electrolysis, a factor that will not only cause pain at the treatment site but also reduces shelf life of the product.

Another choice for the conductive body (61) is stainless steel/polyester fiber. The softness of the mixed fabric is better than that of the aluminum foil but is vulnerable to the electromagnetic interference from nearby electrical appliance. Further, the impedance of such conductive medium can be as high as 30 ohms PSI.

When the conductive body (61) is made of another nonmetal material, carbon film, the advantage is that electromagnetic interference caused by nearby electrical appliance can be avoided. Conventionally, the carbon powder and the plastic film are the fundamental materials to produce the carbon film, wherein the carbon powder is sprayed on the plastic film. However, the carbon film hardness is difficult to snugly attach on protruded body parts such as the knees or the elbows because of the high hardness. The impedance of the carbon film is determined by the quantity of the carbon powder sprayed on the plastic film. Usually, the impedance of such carbon film can be as high as more than several tens ohms PSI. If the quantity of the carbon power is increased to improve the conductivity, the carbon film may be broken during the producing process.

SUMMARY OF THE INVENTION

An objective of the invention is to provide a TENS electrode wherein carbon fiber is the conductive body to provide superior softness and low impedance.

Other objects, advantages, and novel features of the invention will become more apparent from the following detailed description when taken in conjunction with the accompanying drawings.

DETAILED DESCRIPTION OF THE INVENTION

Figure 1:
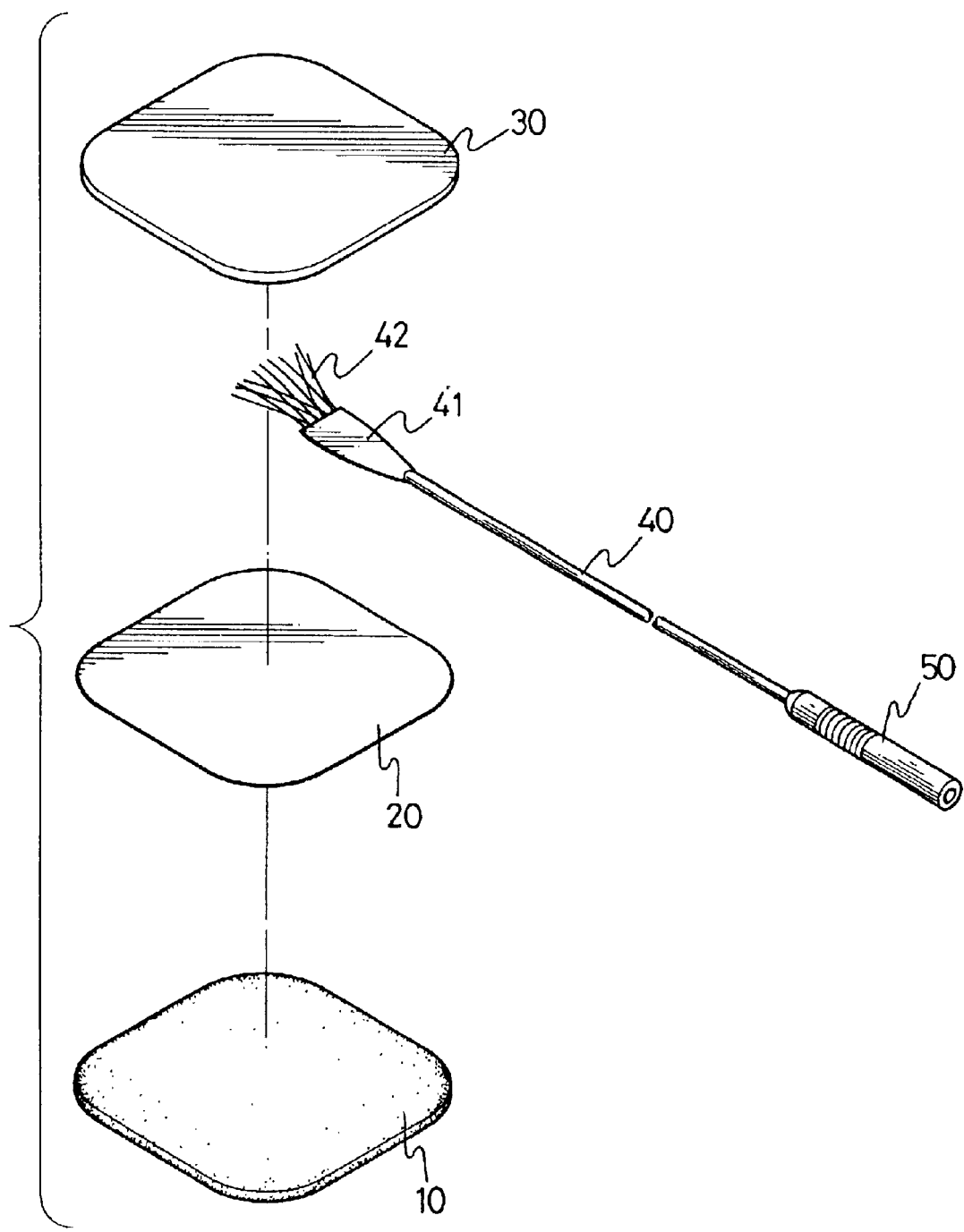
FIG. 1 is an exploded perspective view of a TENS electrode in accordance with the present invention.
Figure 2:
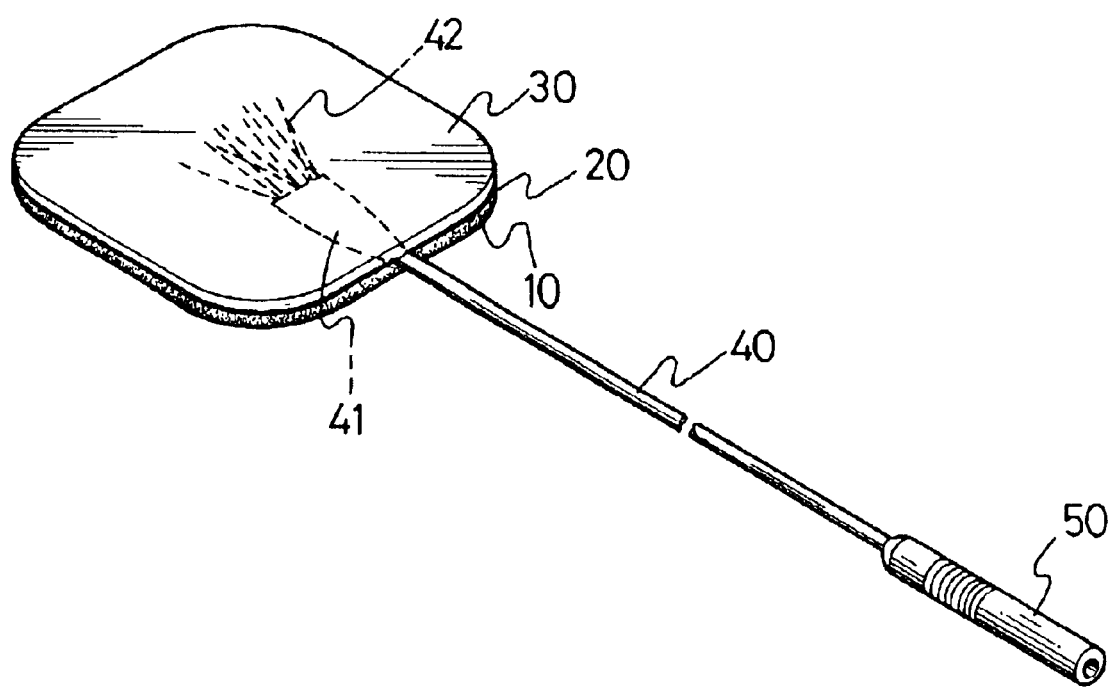
FIG. 2 is a perspective view of a TENS electrode in accordance with the present invention.
Figure 3:
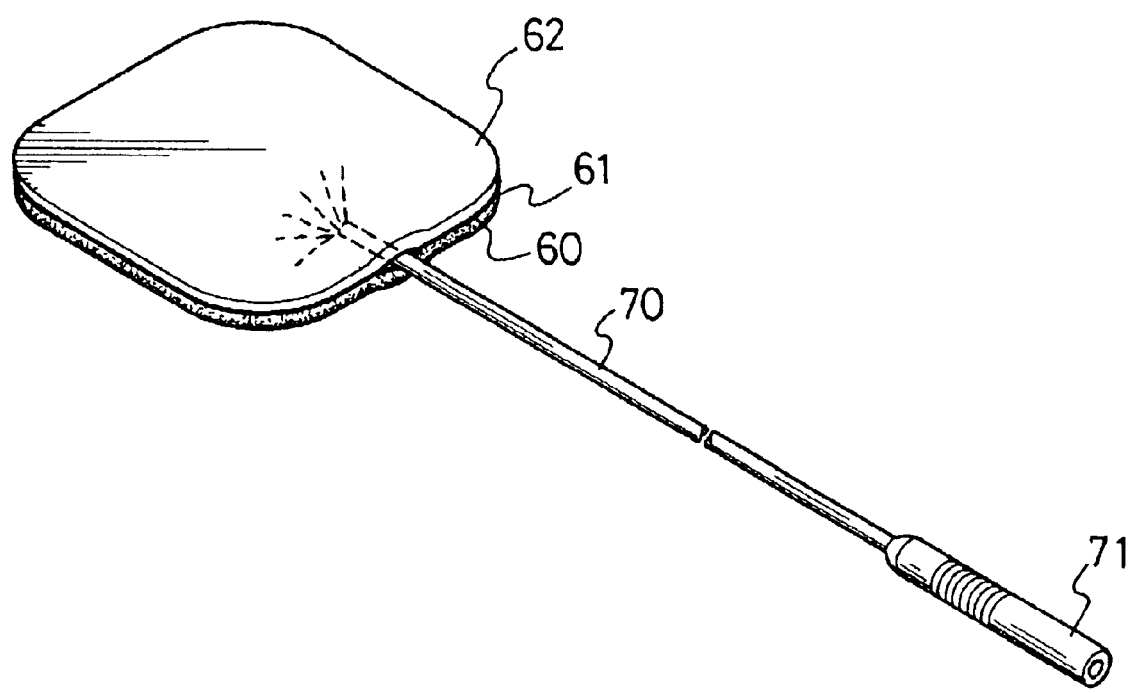
FIG. 3 is a perspective view of a conventional electrode pad.

With reference to FIG. 1, the TENS electrode consists of self-adhesive conductive gel (10) on which the conductive body is mounted (20). An isolating pad (30) is then mounted onto the conductive body (20), and a lead wire (40) with the first terminal securely sandwiched in between the conductive body (20) and the isolating pad (30).

The first terminal of the lead wire (40) is formed as a flat portion (41), wherein conductive cable, such as the carbon strand (42), of the lead wire (40) extends from the flat portion to electrically contact with the conductive body (20). The other terminal of the lead wire (40) is connected with a female joint (50) to link with a TENS (not shown). The patent "tread" design on the flat portion (41) creates friction hence prevents the conductive body (20) from separating the isolating pad (30).

The conductive body (20) is made of carbon fiber. The purposes of carbon fiber are to provide high conductivity, superior softness, to ward off electrolysis, and to avoid any electromagnetic interference. The impedance of carbon fiber is less than 10 ohms PSI, almost the same as that of a metal conductive body. Furthermore, carbon fiber allows the electrode to snuggly fit on any part of the human body.

The invention may be varied in many ways by a skilled maker. Such variations are not to be regarded as a departure from the spirit and scope of the invention, and all such modifications are intended to be included within the scope of the following claims.

What is claimed is:

1. An electrode for a transcutaneious electrical nerve stimulator, the electrode comprising a lawyer of self-adhesive conductive gel onto which a conductive body is mounted, an isolating pad mounted on the conductive body, a lead wire with a first terminal securely sandwiched in-between the conductive body and the isolating pad, wherein the improvement comprises:

the conductive body being made of carbon fiber, whereby the impedance of the conductive body is reduced to less than 10 ohm PSI (per square inch), thus the electromagnetic interference is avoided and the superior softness of the electrode is provided;

the first terminal of the lead wire sandwiched in-between the conductive body and the isolating pad, wherein the first terminal is formed with a flat portion to be securely attached on the conductive body, and a conductive cable expending from the flat portion is electrically contacted with the conductive body.

* * * * *